(12) United States Patent
Christian et al.

(10) Patent No.: US 6,811,019 B2
(45) Date of Patent: Nov. 2, 2004

(54) METHOD AND APPARATUS UTILIZING SERVO MOTORS FOR PLACING PARTS ONTO A MOVING WEB

(75) Inventors: Rebecca Hansen Christian, Montgomery, OH (US); Jeffrey Hale Blumenthal, Anderson, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/682,604

(22) Filed: Oct. 9, 2003

(65) Prior Publication Data

US 2004/0089516 A1 May 13, 2004

Related U.S. Application Data

(63) Continuation-in-part of application No. 09/897,822, filed on Jun. 29, 2001, now Pat. No. 6,705,453.

(51) Int. Cl.[7] .............................................. B65G 17/46
(52) U.S. Cl. ................. 198/471.1; 198/459.8; 198/408; 198/460.1; 198/461.2; 198/472.1; 156/520; 156/521; 156/552; 156/568
(58) Field of Search ........................... 198/459.8, 471.1, 198/472.1, 803.5, 803, 408, 460.1, 461.1, 461.2; 156/552, 567, 568, 519–521

(56) References Cited

U.S. PATENT DOCUMENTS 3,963,557 A * 6/1976 Patterson ..................... 156/519
4,333,790 A    6/1982 Schaffron
4,632,721 A    12/1986 Hoffmann et al.
4,786,046 A  * 11/1988 Freeman et al. ............ 271/276
4,838,982 A    6/1989 Klaeser et al.
4,960,186 A    10/1990 Honda
5,091,039 A    2/1992 Ujimoto et al.
5,104,116 A    4/1992 Pohjola (List continued on next page.)

FOREIGN PATENT DOCUMENTS

| CH | 678616 A5 | 10/1991 |
|---|---|---|
| EP | 0 812 789 A2 | 12/1997 |
| WO | WO 99/46136 A1 | 9/1999 |
| WO | WO 01/00492 A1 | 1/2001 |
| WO | WO 01/53156 A1 | 7/2001 |
| WO | WO 02/07664 A2 | 1/2002 |

*Primary Examiner*—Kathy Matecki
*Assistant Examiner*—Mark A. Deuble
(74) *Attorney, Agent, or Firm*—Jack L. Oney, Jr.; Jay A. Kreebe; Ken K. Patel (57) ABSTRACT

An apparatus and method for receiving a material web traveling at a first speed in a receiving zone, forming discrete parts from the material web, and applying the discrete parts onto a carrier traveling at a second speed through an application zone. The apparatus has a cutting device for severing the material web to form the discrete parts. At least two shells for receiving the discrete parts in the receiving zone and applying the discrete parts in the application zone are used. The shells may be coupled to programmable motors for moving said shell in an orbital path. A roll may be positioned interior to said shells. The cutting device may be used to sever the material web between said shells and against said roll. The roll may be a vacuum roll that provides vacuum in order to hold the discrete parts against said shells.

20 Claims, 10 Drawing Sheets

U.S. PATENT DOCUMENTS

| | | | |
|---|---|---|---|
| 5,116,452 A | 5/1992 | Eder | |
| 5,149,392 A | 9/1992 | Plaessmann | |
| 5,224,405 A | 7/1993 | Pohjola | |
| 5,235,515 A | 8/1993 | Ungipiyakul et al. | |
| 5,286,543 A | 2/1994 | Ungipiyakul et al. | |
| 5,380,381 A * | 1/1995 | Otruba | 156/64 |
| 5,413,651 A * | 5/1995 | Otruba | 156/64 |
| 5,684,344 A | 11/1997 | Takei | |
| 5,693,195 A | 12/1997 | Saito et al. | |
| 5,709,770 A | 1/1998 | Asghar et al. | |
| 5,735,996 A | 4/1998 | Asghar et al. | |
| 5,766,406 A | 6/1998 | Bohn et al. | |
| 5,783,032 A | 7/1998 | O'Callaghan et al. | |
| 5,849,143 A | 12/1998 | Ingalls | |
| 5,888,343 A | 3/1999 | Olson | |
| 5,895,555 A | 4/1999 | Van Den Bergh | |
| 5,932,039 A | 8/1999 | Popp et al. | |
| 5,965,963 A | 10/1999 | Chitayat | |
| 5,994,798 A | 11/1999 | Chitayat | |
| 6,022,443 A | 2/2000 | Rajala et al. | |
| 6,059,710 A | 5/2000 | Rajala et al. | |
| 6,074,333 A | 6/2000 | Rajala et al. | |
| 6,139,004 A | 10/2000 | Couillard et al. | |
| 6,149,755 A | 11/2000 | McNichols et al. | |
| 6,350,070 B1 | 2/2002 | Tasma | |
| 6,431,241 B1 | 8/2002 | Gonzalo | |
| 6,450,321 B1 | 9/2002 | Blumenthal et al. | |
| 2002/0023723 A1 | 2/2002 | Blumenthal et al. | |
| 2002/0029856 A1 | 3/2002 | Gonzalo | |
| 2002/0175047 A1 | 11/2002 | Blumenthal et al. | |
| 2003/0079330 A1 | 5/2003 | Stopher et al. | |
| 2003/0111184 A1 | 6/2003 | Hilt et al. | |

* cited by examiner

Fig. 9

METHOD AND APPARATUS UTILIZING SERVO MOTORS FOR PLACING PARTS ONTO A MOVING WEB

This application is a continuation-in-part of prior application Ser. No. 09/897,822 filed Jun. 29, 2001 now U.S. Pat. No. 6,705,453, published on Feb. 28, 2002. as U.S. patent application Publication No. 2002/0023723A1, and prior application Ser. No. 10/197,023 filed Jul. 17, 2002, published on Nov. 28, 2002 as U.S. patent application Publication No. 2002/0175047A1.

FIELD OF THE INVENTION

The present invention relates to a method and apparatus for receiving a material web traveling at a first speed in a receiving zone, forming discrete parts from the material web, and applying the discrete parts onto a carrier traveling at a second speed through an application zone.

BACKGROUND OF THE INVENTION

Disposable absorbent articles, such as disposable diapers, generally, have been manufactured by a process where discrete parts or components of different materials, such as leg elastic, waist elastic, tapes and other fasteners have been applied to a continuously moving carrier. Often, the speed at which the parts are fed from one place in the process onto a carrier is different from the speed of the carrier; therefore, the speed of the parts must be changed to match the speed of the carrier to properly apply the parts without adversely affecting the process or the finished product.

Similarly, labels are typically placed onto articles when the speed at which the labels are fed into the process is not the same as the speed of the article to be labeled. Thus, the speed of the labels must be changed to match the speed of the carrier to properly apply the parts without adversely affecting the process or the finished product.

Several different conventional methods for changing the speed of a part or component of material such that it can be applied to a continuously moving carrier have been known to those skilled in the art.

For example, one known method is commonly referred to as the "slip cut" or "cut and slip" method. A web of material, which is traveling at a slower speed than the carrier, is fed into a knife and anvil roll having a surface speed equal to speed of the carrier. The material slips against the surface of the anvil roll until the knife cuts it into discrete parts. The purpose of the slip is to ensure the correct amount of material is metered into the system at the desired tension prior to cutting. As the material is cut into the discrete parts, vacuum in the anvil roll is activated to hold the discrete part on the anvil without slipping, so that the discrete part is accelerated to the speed of the anvil roll. The anvil roll then carries the part to the point where the vacuum is released and the parts are applied to the carrier while both the parts and the carrier are traveling at the same speed. The problem with the above method is that the slip process is very sensitive to material properties and process settings. For example, when the coefficient of friction between the material and anvil roll is too high, the material will elongate during the slip process. This elongation, if it occurs, can contribute to high variability in the final cut length and placement of the discrete part on the carrier.

Another method has used festoons to reduce the speed of the carrier to match the speed of the discrete parts of material to be applied to the web. An example of this method is described in U.S. Pat. No. 5,693,195 issued to Schmitz. The carrier is temporarily slowed down to the speed of the parts with the excess portion of the carrier gathering in festoons. The parts of material are then applied to the carrier while both the parts and the web are traveling at the same speed. The festoons are then released allowing the moving web to return to its original speed. This method has two main drawbacks. First, the carrier must be festooned and then released; this may damage or otherwise change the properties of the carrier. Second, the storage system requires a large amount of space in typical disposables production systems because there is a direct relationship between line speed and storage space needed.

Another method has utilized a cam actuated follower arm. The cam actuated follower comprises a cam follower at one end of the arm and a holding plate at the other end of the arm. The cam follower remains in contact with a fixed cam which is mounted concentric with the instantaneous center of rotation of the holding plate. As the holding plate rotates, its radial distance from the center of rotation is increased and decreased to change the surface speed of the holding plate. The discrete parts of material are placed on the holding plate when it is at its smallest radius so that the speeds match. The plate then extends radially enough during the rotation to match the speed of the plate to the speed of the carrier. At this point the discrete parts are transferred to the carrier. This method has two main drawbacks. First, the plate is designed to match the curvature of one radius, not both. This means that either the pick-up of the discrete part or the transfer of the discrete part, or both, will occur across a gap for some part of the transfer. This can lead to a loss of control of the discrete part, which impacts handling of parts under tension, such as leg elastics. Second, to achieve the desired change in speed, the mechanical elements typically used, such as cams or linkages, become fairly large to stay within acceptable design limits for accelerations and rise angles. This size leads to increased cost and reduced flexibility, as the unit must be redesigned for each application.

Another method has utilized noncircular gears to change the speed of a transferring device. The means rotate at a constant radius, but the rotational velocity is varied between a minimum and a maximum to pick up the discrete part at its speed and place the part on the carrier at its speed. This eliminates the size issues and speed or gap mismatch issues, but relies on mechanical means to achieve the change in rotational velocity. The drawback of this is that new transmission parts (gears or other means) are required each time a change in product design occurs that changes placement pitch length, discrete part length, or other key factors. This can be expensive and time-consuming to change. An example of this method is described in U.S. Pat. No. 6,022,443 issued to Rajala and Makovec.

Another method is commonly referred to as a servo part placer. This apparatus functions, similar to the cut-and-slip method described above except that it attempts to match a first speed of the material web when receiving the part and a second speed when placing the part onto a carrier. In a first prior art embodiment, a cutting blade is used to sever the material web against an anvil roll and then the anvil roll transfers the discrete part to a transfer head for subsequent application onto the carrier. While the use of anvil roll, instead of severing against transfer heads, allows for the transfer heads to be more lightweight, the use of anvil roll has difficulties in the continuous application of adhesive to the material web because the discrete part would adhere to the transfer head. In a second prior art embodiment, a cutting blade is used to sever the material web directly against a transfer head and the transfer head then applies the discrete part to the carrier. While this embodiment allows for the continuous application of adhesive to the material web, it does sever against the transfer heads which requires them to be sufficiently rigid (and ultimately heavy) to sustain the impact of cutting blade. Consequently, the heavier transfer heads create higher inertia that ultimately requires the use of high torque motors.

What is needed is a servo part placer apparatus that is capable of continuous application of adhesive to the material web and which does not sever against the transfer heads (herein referred to as shells) such that smaller motors that fit well into the apparatus' mechanical design may be used.

SUMMARY OF THE INVENTION

An apparatus and method for receiving a material web traveling at a first speed in a receiving zone, forming discrete parts from the material web, and applying the discrete parts onto a carrier traveling at a second speed through an application zone. The apparatus has a cutting device for severing the material web to form the discrete parts. At least two shells for receiving the discrete parts in the receiving zone and applying the discrete parts in the application zone are used. The shells may be coupled to programmable motors for moving said shell in an orbital path. The programmable motors and shells may be aligned in relation to a common axis. The programmable motors maintain said shells at first surface speeds in the receiving zone as said shells pick up the discrete parts and maintain said shells at second surface speeds in the application zone as said shells apply the discrete parts to the carrier. A roll may be positioned interior to said shells. The cutting device may be used to sever the material web between said shells and against said roll. The roll may be a vacuum roll that provides vacuum in order to hold the discrete parts against said shells. The cutting device may be a cutting roll having an adjoining cutting blade which together rotate with or about a cutting roll shaft. The cutting device may rotate at a cutting surface speed substantially equal to a velocity of the material web while each of the discrete parts are being severed and formed and at a different cutting surface speed during intervals between discrete parts being severed and formed from the material web.

The first surface speeds of said shells may be substantially equal to the first speed of the discrete parts in the receiving zone and the second surface speeds of the shells may be substantially equal to the second speed of the carrier in the application zone. Additionally, the first and second surface speeds of said shells may be substantially constant. Alternatively, the first and second surface speeds of said shells may be variable. Alternatively, either the first surface speeds of said shells or the second surface speeds of said shells may be variable.

The programmable motors may be a programmable motor selected from the group consisting of a motor having a hollow shaft, a linear motor having a stationary track rail, a motor having a rotatable outer rotor and a stationary inner stator, and a motor having a rotor rotatable around a stationary component of a motor. The programmable motors are located on at least one stationary central shaft coaxially with the common axis.

The shells may have an axial length from about 4 cm to about 200 cm, tangential width from about 0.5 cm to about 200 cm, and a thickness from about 0.25 mm to about 3 mm. The shells may be constructed from materials including, but not limited to, plastic, aluminum, steel, and combinations thereof. The shell may hold the discrete parts by vacuum, mechanical forces, electrostatic forces, magnetic forces, and combinations thereof.

An applicator for performing a secondary process on the parts between the receiving zone and the application zone may be used. An applicator for performing a secondary process on the parts before the receiving zone may also be used. The secondary process may be the application of adhesive or printing.

The carrier may be selected from the group consisting of a web substrate, belt, drum, and external-discrete part.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify like elements and numbers with the same final two digits indicate corresponding elements among embodiments, wherein:

DETAILED DESCRIPTION OF THE INVENTION

Reference will now be made in detail to various exemplary embodiments of the invention, several of which are also illustrated in the accompanying drawings.

The present invention provides a method and apparatus for receiving a material web traveling at a first speed in a receiving zone, forming discrete parts from the material web, and applying the discrete parts onto a carrier traveling at a second speed through an application zone. The apparatus and method are particularly useful for applying any discrete part to a carrier useful in the making of disposable absorbent articles or for placing labels onto articles. It is readily apparent, however, that the method and apparatus would be suitable for applying any part to a substrate web or carrier of parts.

Figure 1:
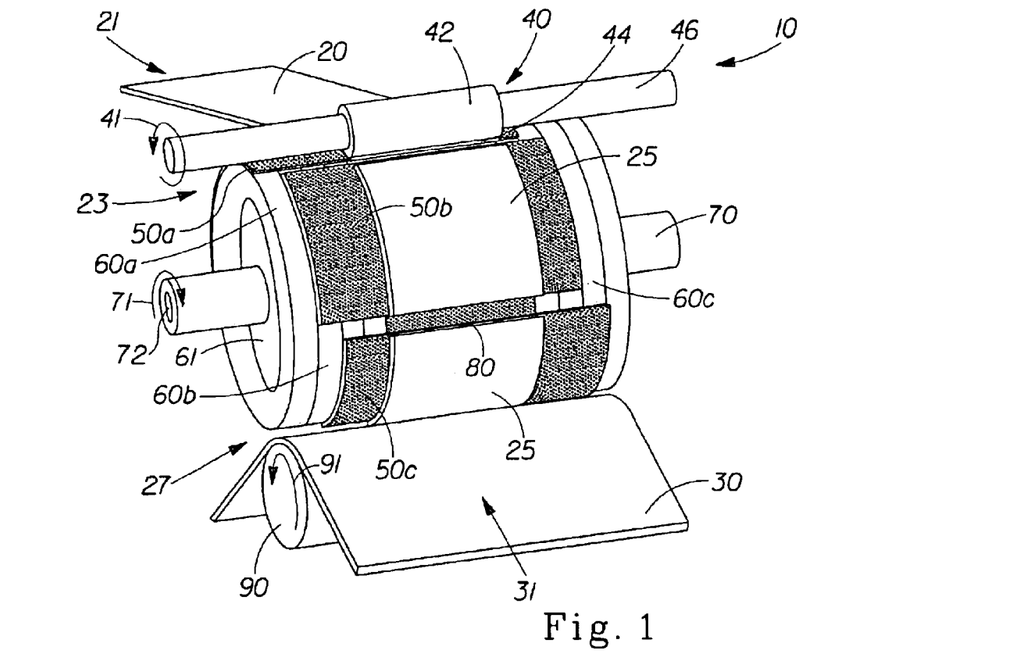
FIG. 1 representatively shows a front perspective view of an exemplary apparatus of the present invention.
Figure 2:
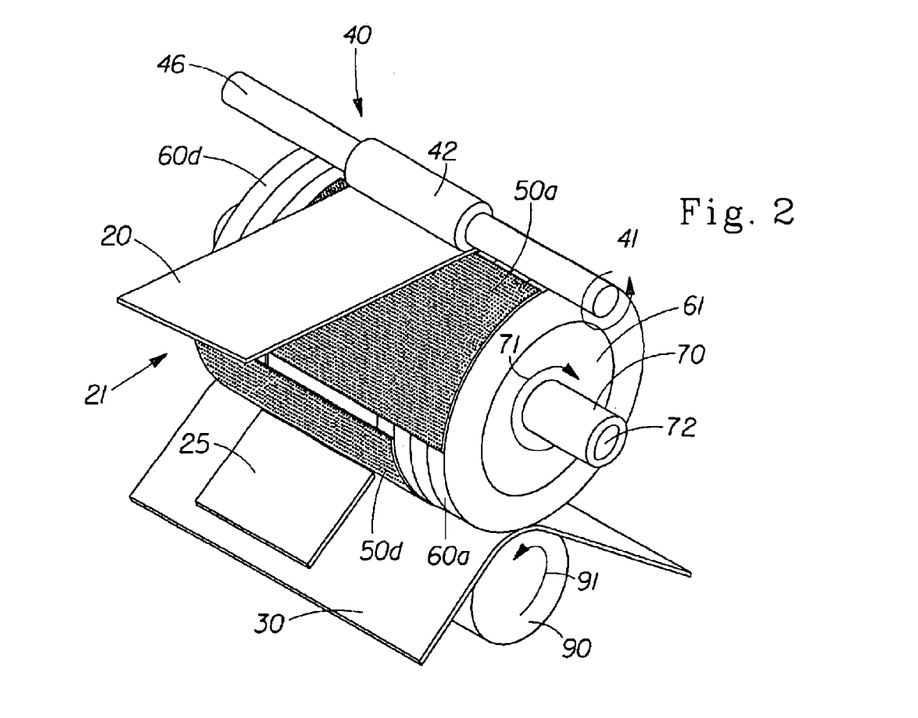
FIG. 2 representatively shows a rear perspective view of the apparatus in FIG. 1.
Figure 3:
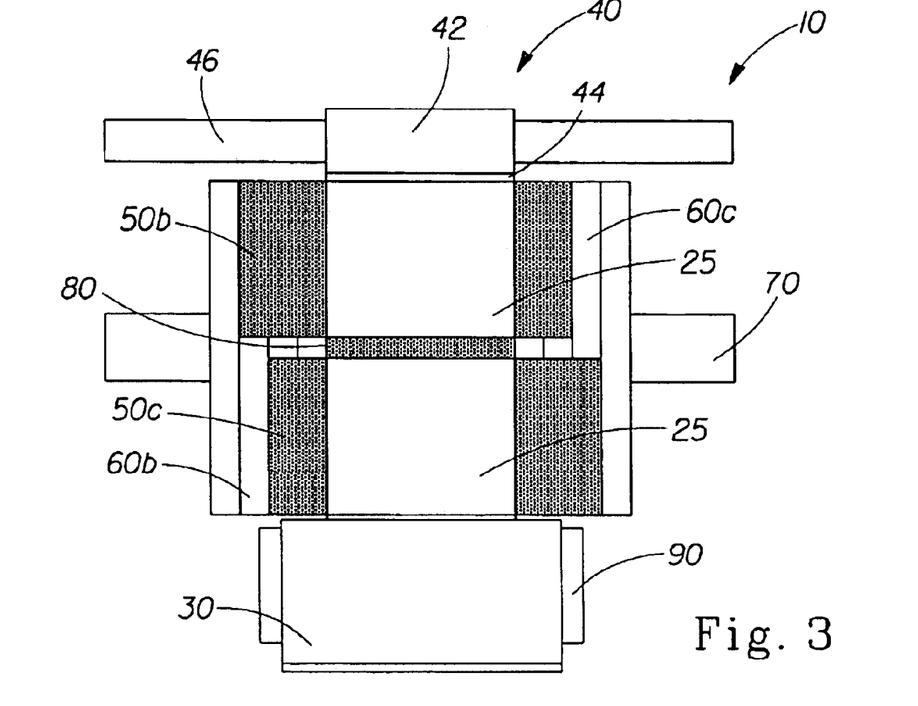
FIG. 3 representatively shows a front elevational view of the apparatus in FIG. 1.

FIGS. 1–3 depicts a non-limiting exemplary embodiment of an apparatus 10 for receiving a material web 20 traveling at a first speed in a direction indicated by arrow 21, making discrete parts 25 from the material web, 20, and then applying the discrete parts 25 to a carrier 30 traveling at a second speed in a direction indicated by arrow 31. Carrier 30 may include, but is not limited to, a web substrate, belt, drum, and external-discrete part (i.e., discrete part not formed from material web 20). Apparatus 10 includes a cutting device 40 for cutting material web 20 and thus making discrete parts 25. More particularly, cutting device 40 has a cutting roll 42 having an adjoining cutting blade 44 which together rotate with or about a cutting roll shaft 46 in a rotational direction indicated by arrow 41. Cutting blade 44 severs material web 20 against a roll 80. Thus, the material web 20 is cut into discrete parts 25 in the receiving zone 23 (generally defined as that area in close proximity to the cutting device 40) and then later transferred by a shell 50 to the application zone 27 (generally defined as that area in close proximity to where discrete parts 25 are applied to carrier 30). It should be noticed that cutting blade 44 does not sever material web 20 against shell 50*a*, rather against roll 80. Because shell 50*a* is not cut against, shell 50*a* may be lightweight and thin. This aspect of the invention will be discussed later.

In this non-limiting exemplary embodiment of apparatus 10, four shells 50*a–d* are used, however, one skilled in the art would appreciate that any reasonable number of multiple shells may be used. Shells 50*a–d* are adjoined to a corresponding motor (or motor pair; used herein interchangeably) 60*a–d* that rotates said shell about a shell shaft 70 in a rotational direction as indicated by arrow 71. In this exemplary embodiment, shells 50*a–d* have an axial length from about 4 cm to about 200 cm, tangential width from about 0.5 cm to about 200 cm, and a thickness from about 0.25 mm to about 3 mm. Shells 50*a–d* may be constructed of plastic, aluminum, steel, and combinations thereof; although one skilled in the art would appreciate that other suitable materials may be used. The dimensions of the shell 50 may vary depending upon the desired output of the apparatus 10 and the size and shape of the discrete parts 25 being transferred. As motor 60 rotates, the shells 50 travel in the direction indicated by the arrow 71 as shown in FIGS. 1 and 2. The circumferential, outer peripheral surface of the shell 50 defined by an outer radius, travels along and defines an orbital path that passes through a receiving zone 23 and an application zone 27. The receiving zone 23 and the application zone 27 are defined by the respective regions of the orbital path traveled by the shell 50. The size and shape of the shells 50 may vary. For example, if the apparatus 10 includes four shells 50*a–d*, as illustrated in FIGS. 1 and 2, each shell 50 may have an outer peripheral arc length which spans from about 2 to about 89 degrees of the orbital path.

The use of a programmable motor in apparatus 10 provides an inexpensive and adaptable method for receiving parts 25 traveling at a speed and applying the parts to a carrier 30 traveling at a different speed. The variable angular velocity is produced by varying the current supplied to the motor 60. Since the shell 50 is coupled to the output of the motor 60, changes in the angular velocity and position of the motor 60 directly correlate to changes in the angular velocity and position of shell 50. The current supplied to the motor 60 can be controlled using any of a variety of a methods for programming motors known to those skilled in the art such as, standard cam curve functions, a reference data table containing reference points, desired motor encoder points, and the like or combinations thereof.

The means of supplying the rotational movement required can be achieved in a plurality of methods to those skilled in the art. The programmable electric motors can be driven from any known power source that is capable of delivering a modulated signal such that the motor torque can be varied proportionally. The number of motors 60 included per shell 50 can be any suitable number. Each motor 60 attached to a single shell 50 can be supplied by one or more power sources capable of delivering a modulated torque signal. The torque signal is typically an electrical current which may be fed to the individual motors 60 by separate power supplies or by a single power supply and controlled by a plurality of methods to those skilled in the art.

As compared to conventional methods for changing the speed of a discrete part so that it can be applied to a continuously moving carrier (such as a slip-and-cut known in the art), the use of programmable motors provides the ability to obtain greater changes in speed and to maintain constant speeds for a fixed duration. The fixed speed dwell achieved by programmable motors can be accurately and quickly generated to control the length and placement of the parts. In comparison to the noncircular gear method described in the background section above, the use of programmable motors provides the ability to change the profile at will without requiring the fabrication of new parts.

The actual position of the shell 50 can be controlled by a plurality of methods known to those skilled in the art including, but not limited to, a position transducer (e.g., encoder-based system, resolver-based system, etc). For instance, the actual position of the shell 50 can be controlled by a programmable system that incorporates a position feedback from the shell 50 and motor 60. Alternatively, the actual position may not be needed if the position of the shell 50 can be inferred by other means known to those skilled in the art. Irrespective of the type of control method used, the control method may be used to provide the proportional signal to the motor power supplies that will generate the modulated torque signal. A control system may or may not be integrated into the motor power supply. A control system, along with the motor power supply, may or may not be integrated into the motor 60 itself. A control system may or may not be digitally controlled, and may be constructed in various methods, and configurations known to those skilled in the art. The control system, power supplies, feedback devices, and motor devices, and any other components required for the purpose of providing rotational movement are hereafter referred to as the "drive system" for shells 50.

The drive system (not shown) may be capable of continuously controlling the position of the shell 50, and allowing the shell to stay in phase to a given position on the recipient product, web, or host machine. The drive system may be capable of following speed transitions or positions variations on the recipient product or web, by phasing itself, when necessary, to the recipient product, web, or host machine, with or without operator intervention. The drive system will allow for the registration of the discrete part 25 on shell 50 in relation to the carrier 30, either upstream or downstream of shell 50.

The drive system may be capable of providing for a plurality of control methods and algorithms known to those skilled in the art for the purpose of providing motion and position control that will allow the transfer of a discrete part 25 to a recipient product or web. The drive system may be capable of changing the part length with or without operator intervention, for the purpose of varying product sizes or continuous part length, or position variation control. The position reference for the drive system may be a pre-calculated cam profile, continuously calculated profile, or any positional trajectory generation algorithm known to those skilled in the art, and may be either digital or analog based. The motion trajectory for shell 50 may be based on a pre-calculated profile or a profile that is modified by the speed of the recipient product or web.

Motor 60 may be a programmable motor selected from the group consisting of a motor having a hollow shaft, a linear motor having a stationary track rail, a motor having a rotatable outer rotor and a stationary inner stator, and a motor having a rotor rotatable around a stationary component of a motor. In an exemplary embodiment, motors 60a–d may be an outer rotor motor, wherein, the outer portion (e.g., larger disc-like structure) serves as the rotor (i.e., spins) and the inner portion (e.g., smaller disc-like structure 61) serves as the stator (i.e., stationary). The stator is placed around shell shaft 70. In this exemplary embodiment, a pair of outer rotor motors is used to rotate a single shell 50 and thus support shell 50 on its longitudinal ends; although one skilled in the art would appreciate that other arrangements of motor(s) to shell(s) may be used.

Shells 50a–d may further include a gripping mechanism so that the outer concave surface of the shell can capture a discrete part 25 in the receiving zone 23 and transport it to the application zone 27. Said gripping mechanism may be vacuum, electrostatic forces, mechanical forces (e.g., clamps) or another suitable method known in the art. In this exemplary embodiment, shells 50a–d may be air pervious such that vacuum may be applied by a roll 80 which is positioned interior to said shells. The vacuum force helps to keep discrete parts 25 positioned against shells 50a–d. Vacuum pressure may be applied over the entire circumference of roll 80 or it may also be selectively applied from the receiving zone 23 to the application zone 27. Vacuum pressure is created through roll 80 by applying vacuum pressure through a connected hollow portion 72 in shell shaft 70. A vacuum supply line (not shown) may then be attached to shell shaft 70 using existing pipe connector technology (e.g., rotary pipe connectors).

Discrete parts 25 are applied to carrier 30 in the application zone 27. At such time, it may be desirable to discontinue the vacuum force. A backing roll 90 may be used to help bring carrier 30 in close proximity to application zone 27 for transferring of discrete parts 25. Other known techniques to assist the transferring of discrete parts 25 to carrier 30 may be appreciated by one skilled in the art including, but not limited to, adhesive applied on discrete part 25, adhesive applied on carrier 30, electrostatic charge between the discrete part 25 and carrier 30, vacuum on the carrier 30, blown air to blow discrete part 25 off of shell 50, and the like or combinations thereof. Alternately, the transfer can include the generation of a weld between the discrete part 25 and the carrier 30 by any of a variety of means known to those skilled in the art including, but not limited to, pressure generation at a nip formed between the shell 50 and backing roll 90 at transfer, interaction between a pattern on the shell 50 and an ultrasonic horn behind the carrier 30 at transfer, and the like, or combinations thereof. In addition, in order to aid the welding process, the discrete part 25 may be modified on the shell 50 by energy addition using any mechanism known to those skilled in the art including, but not limited to, hot air currents, ultraviolet lighting, laser bombardment and the like or combinations thereof.

Figure 4:
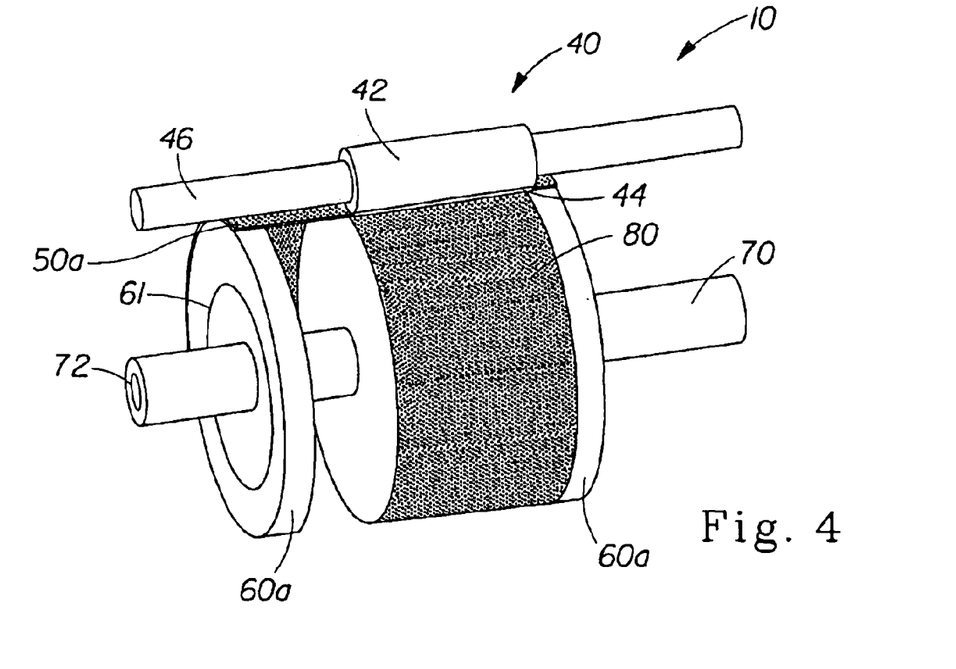
FIG. 4 representatively shows a front perspective view of the apparatus in FIG. 1, wherein, the shells are removed to illustrate the vacuum roll that is positioned underneath them.
Figures 5A, 5B, 5C, 5D:
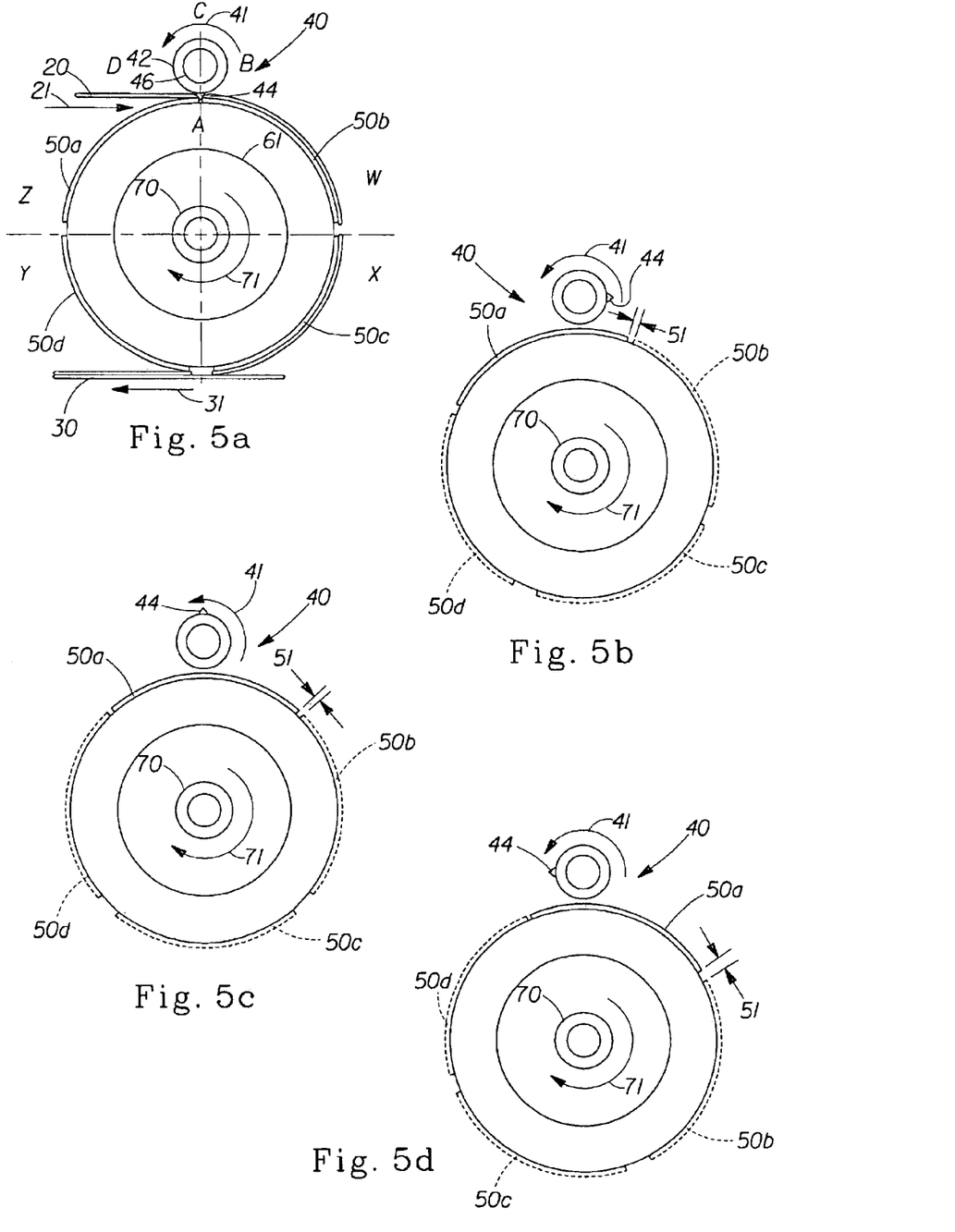
FIG. 5a representatively shows a schematic view of the apparatus in FIG. 1, wherein, the cutting blade is in position A and shell 50a is significantly positioned in quadrant Z.
FIG. 5b representatively shows a schematic view of the apparatus in FIG. 1, wherein, the cutting blade is in position B and shell 50a is significantly positioned in quadrant Z.
FIG. 5c representatively shows a schematic view of the apparatus in FIG. 1, wherein, the cutting blade is in position C and shell 50a is significantly positioned in quadrant W.
FIG. 5d representatively shows a schematic view of the apparatus in FIG. 1, wherein, the cutting blade is in position D and shell 50a is significantly positioned in quadrant W.
Figures 5E, 5F, 5G, 5H:
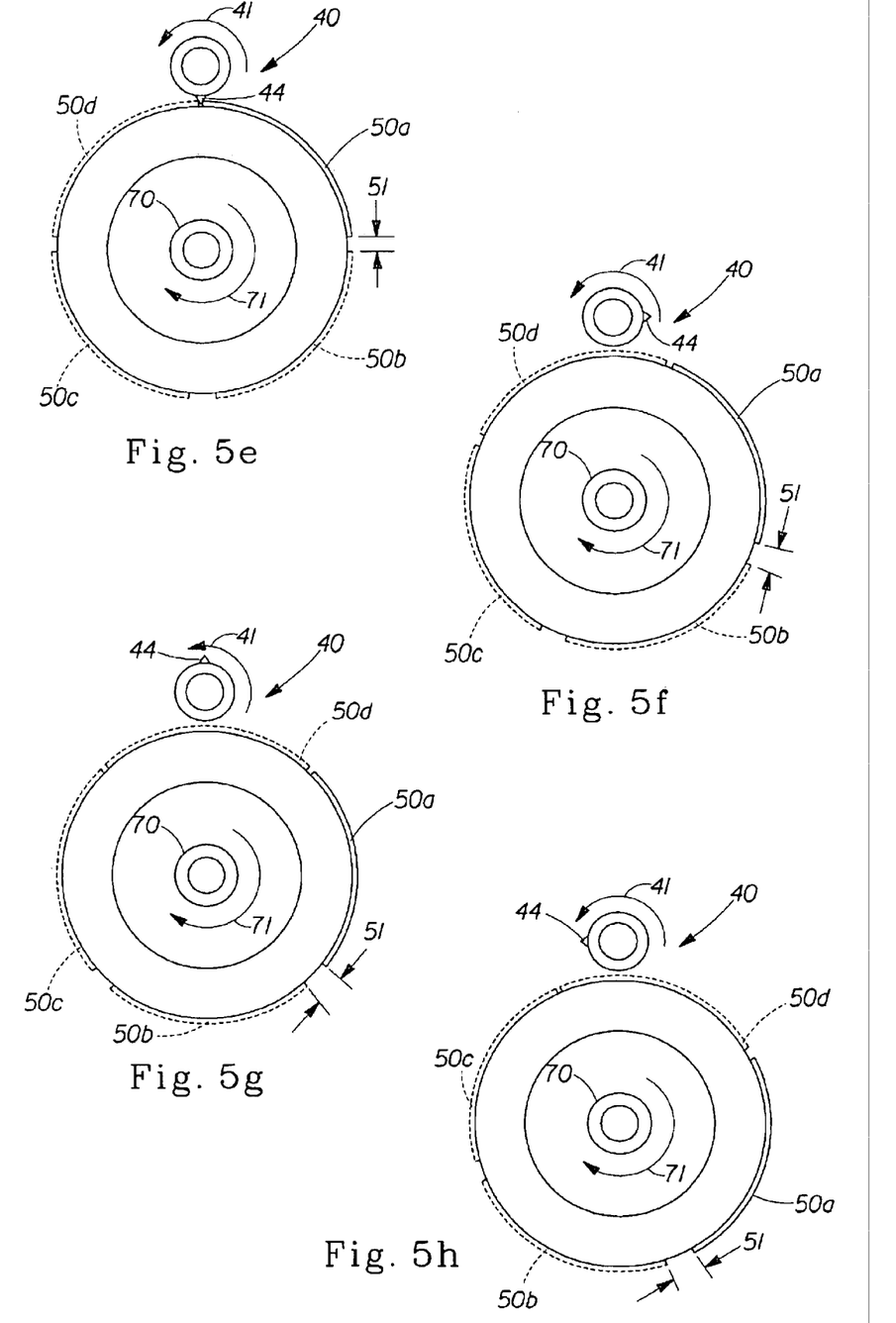
FIG. 5e representatively shows a schematic view of the apparatus in FIG. 1, wherein, the cutting blade is in position A and shell 50a is significantly positioned in quadrant W.
FIG. 5f representatively shows a schematic view of the apparatus in FIG. 1, wherein, the cutting-blade is in position B and shell 50a is significantly positioned in quadrant W.
FIG. 5g representatively shows a schematic view of the apparatus in FIG. 1, wherein, the cutting blade is in position C and shell 50a is significantly positioned in quadrant X.
FIG. 5h representatively shows a schematic view of the apparatus in FIG. 1, wherein, the cutting blade is in position D and shell 50a is significantly positioned in quadrant X.
Figures 5I, 5J, 5K, 5L:
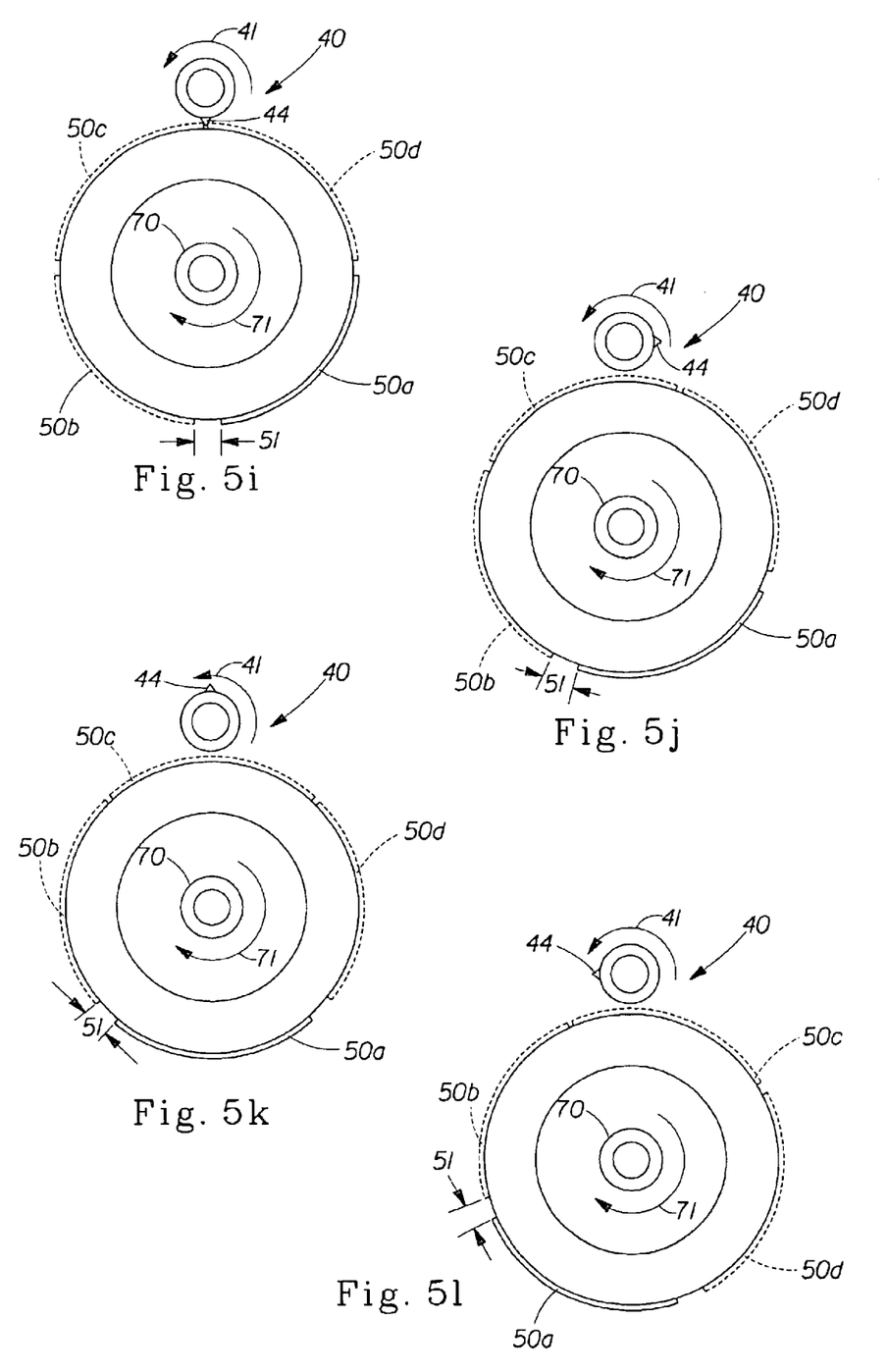
FIG. 5i representatively shows a schematic view of the apparatus in FIG. 1, wherein, the cutting blade is in position A and shell 50a is significantly positioned in quadrant X.
FIG. 5j representatively shows a schematic view of the apparatus in FIG. 1, wherein, the cutting blade is in position B and shell 50a is significantly positioned in quadrant X.
FIG. 5k representatively shows a schematic view of the apparatus in FIG. 1, wherein, the cutting blade is in position C and shell 50a is significantly positioned in quadrant Y.
FIG. 5l representatively shows a schematic view of the apparatus in FIG. 1, wherein, the cutting blade is in position D and shell 50a is significantly positioned in quadrant Y.

Referring to FIG. 4, apparatus 10 is shown with shells 50b–d removed so that roll 80 is more visible. However, shell 50a is still visible and shown as being positioned behind and adjacent to cutting blade 44 which is in the engaged position. As will be further explained and appreciated in FIG. 5, cutting blade 44 does not cut web material 20 against shell 50; rather, cutting blade 44 cuts web material 20 between each shell 50a–d against roll 80.

Figures 5M, 5N, 5O, 5P:
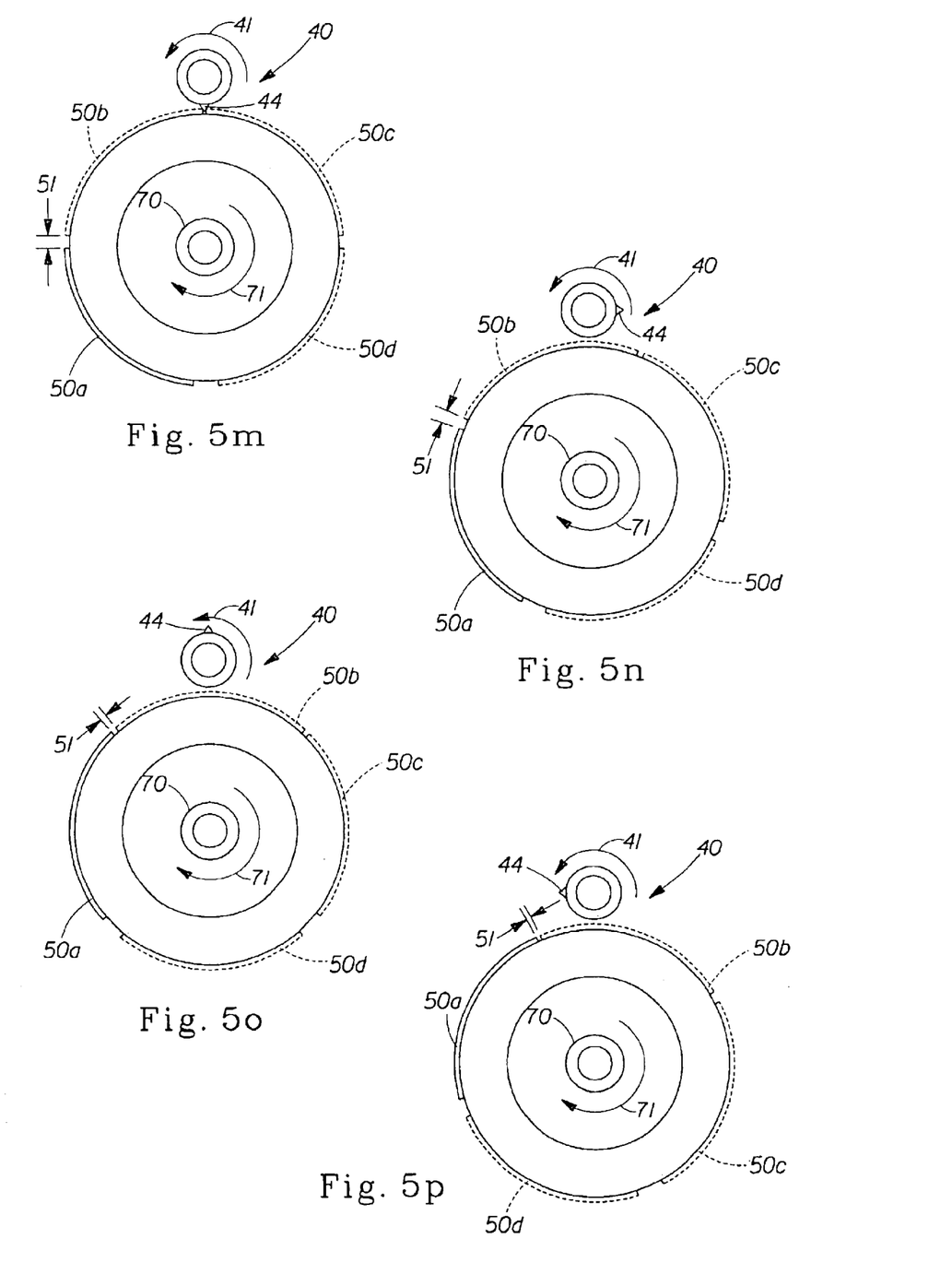
FIG. 5*m* representatively shows a schematic view of the apparatus in FIG. 1, wherein, the cutting blade is in position A and shell 50*a* is significantly positioned in quadrant Y.
FIG. 5*n* representatively shows a schematic view of the apparatus in FIG. 1, wherein, the cutting blade is in position B and shell 50*a* is significantly positioned in quadrant Y.
FIG. 5*o* representatively shows a schematic view of the apparatus in FIG. 1, wherein, the cutting blade is in position C and shell 50*a* is significantly positioned in quadrant Z.
FIG. 5*p* representatively shows a schematic view of the apparatus in FIG. 1, wherein, the cutting blade is in position D and shell 50*a* is significantly positioned in quadrant Z.

FIGS. 5a–5p depict a series of schematic views of apparatus 10 to illustrate the positional relationship between cutting blade 44 and shells 5a–d. Referring now to FIG. 5a, apparatus 10 is first sectioned into four quadrants (W, X, Y and Z). These quadrants will be used to refer to the position of shell 50a. Next, cutting device 40 has been assigned with four position labels (A, B, C and D). These labels will be used to refer to the position of cutting blade 44. These quadrants and labels will be used in FIGS. 5a–5p, however, they are not depicted in each figure in order to keep them visibly pleasing. Shells 50b–d have been dotted-lined so as to focus attention to shell 50a for purposes of communication only. In FIG. 5a, shell 50a is significantly positioned (i.e., more than 50%) in quadrant Z and substantially behind cutting blade 44 as it rotates as indicated by arrow 71.

Material web 20 enters apparatus 10 within quadrant Z. Cutting blade 44 at position A severs material web 20 against the roll 80. It is in this step that the leading edge of the next discrete part 25 is formed. It should be noticed that cutting blade 44 does not sever material web 20 against shell 50a (also refer to FIG. 4). Because shell 50a is not cut against, shell 50a may be lightweight and thin. This aspect of the invention will be further explained and appreciated in reference to FIGS. 6–8. Referring now to FIG. 5b, cutting blade 44 has moved to position B and shell 50a has begun to move into quadrant W. Observe that a shell distance 51 between shell 50a and shell 50b is relatively short at this stage but begins to lengthen through FIG. 5h until such time that shell 50a is positioned near the application zone 27. Conversely, shell distance 51 shortens from FIGS. 5i through 5p until such time that shell 50a is positioned near the receiving zone 23. This increase and decrease in shell distance 51, and corresponding increase and decrease in the rotational velocity of shells 50 is further discussed and appreciated in FIGS. 6 and 7. Referring back to FIG. 5b, cutting blade 44 is now in position B after severing material web 20. Cutting blade will continue through positions C and D in FIGS. 5c and 5d, respectively, and will ultimately return to sever the trailing edge of discrete part 25 (not shown) in FIG. 5e. Cutting blade 44 will repeat this cycle a total of four times (once per each shell) before returning to a similar configuration as represented in FIG. 5a.

Figure 6:
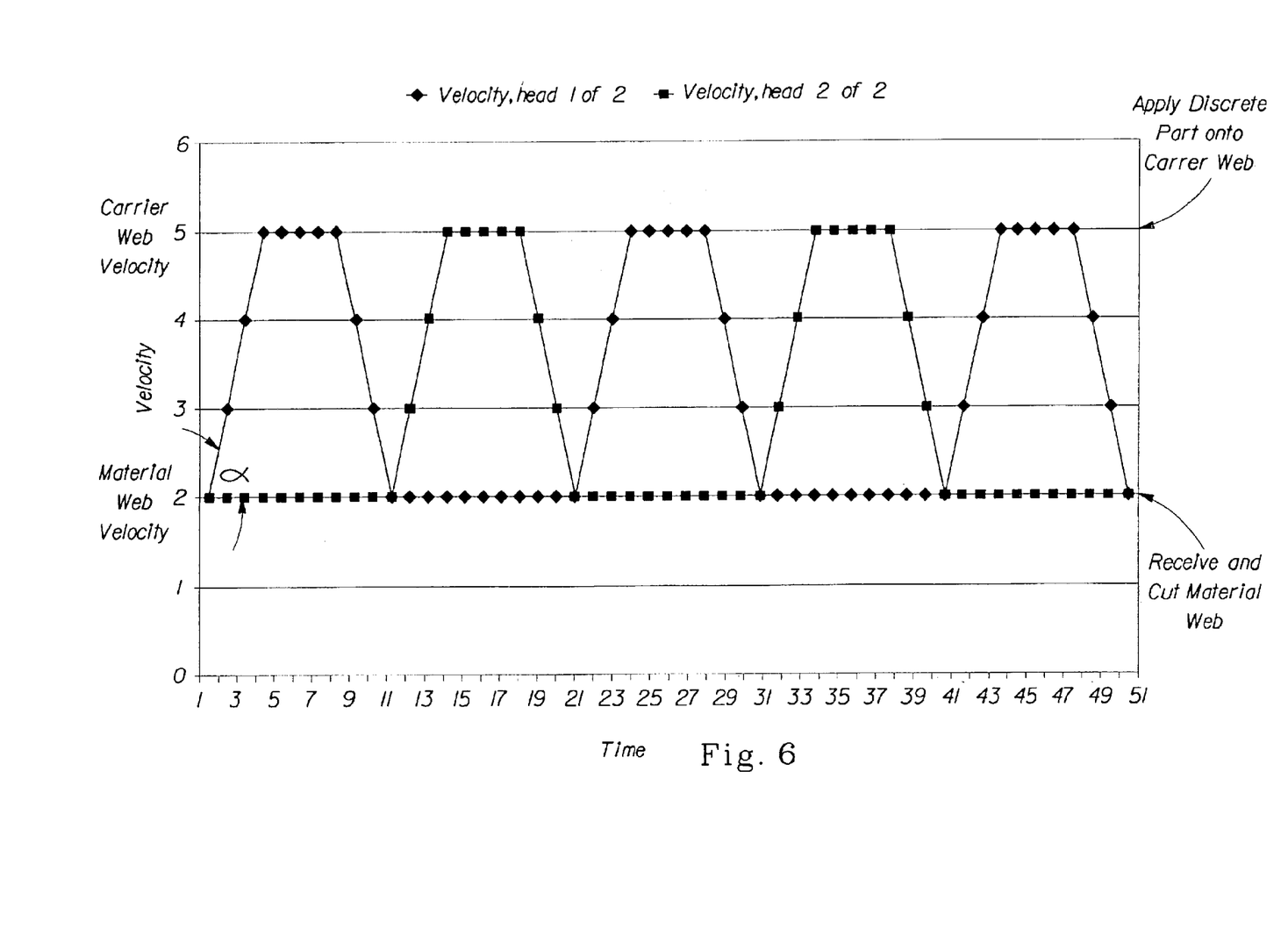
FIG. 6 representatively shows a speed profile for the apparatus in FIG. 1, wherein, two shells are used.
Figure 7:
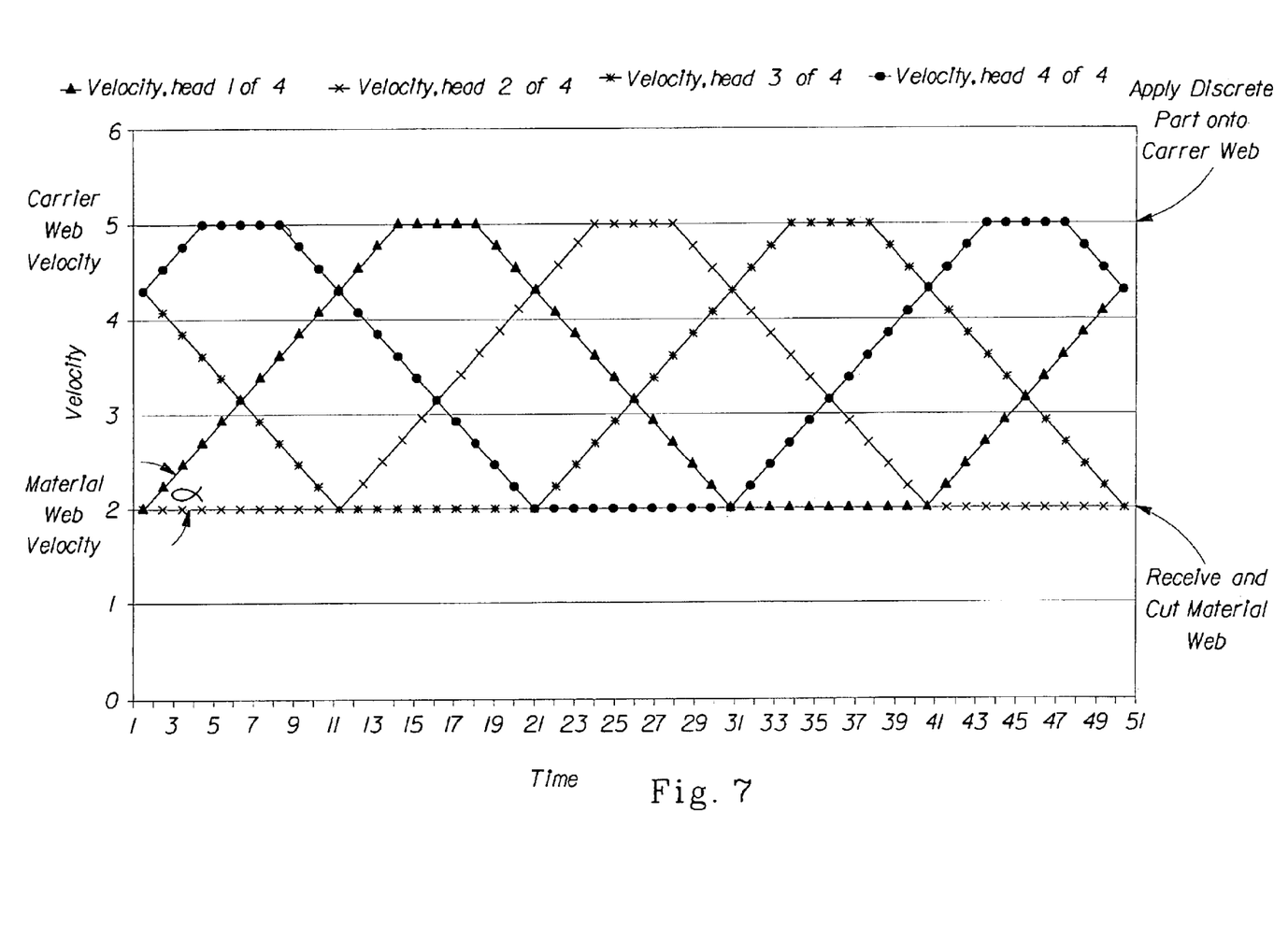
FIG. 7 representatively shows a speed profile for the apparatus in FIG. 1, wherein, four shells are used.

Referring to FIG. 6, a speed profile of an apparatus 10 having two shells 50 is shown to illustrate the increase and decrease in rotational velocity (i.e., angular velocity) of said shells. In one such embodiment, the web material 20 is traveling at a first speed and the carrier 30 is traveling at a second speed, wherein, the first speed is slower than the second speed (i.e., the material web 20 is slower than the carrier 30). To ensure proper transfer of discrete part 25 during the receiving zone 23 and the application zone 27, the speed of shells 50 are varied to match both the material web 20 and the carrier 30 respectively. In this exemplary embodiment, during the receiving of discrete part 25 from the material web 20, shell 50 has a matching velocity of 2 (no particular units). During the application of discrete part 25 onto carrier 30, shell 50 has a matching velocity of 5 (no particular units; the values and ratios of the velocities, accelerations and times are non-limiting such that one skilled in the art would appreciate a variety of values and ratios to meet a particular purpose). Because the discrete parts 25 are made from a continuous material web 20, shells 50 must be continuously sequential in their receiving of discrete parts 25 (as illustrated by the continuous horizontal line at velocity 2). Conversely, because the discrete parts 25 are spaced apart when applied to the carrier 30, shells 50 need not be continuously sequential in their application of discrete parts 25 (as illustrated by the discontinuous horizontal line at velocity 5). In order to meet the necessary dynamics of the receiving and application stages, shells 50 must increase and decrease velocity relatively quickly, as illustrated by the slope angle α. Moving shells 50 in such a manner provides a technical challenge in that the motors which rotate shells 50 may experience a significant amount of acceleration which leads to higher torque. To provide more torque in order to achieve higher line speeds, sometimes larger motors are used. However, herein, using a larger sized motor is not a desired option because increasing the diameter of the motor would also increase the outer radius of shells 50. Increasing the outer radius of shells 50 then increases the length of travel for each shell 50, which then increases the ramping (i.e., acceleration, slope angle α) of rotational velocity, which then increases torque if inertia is held constant. FIG. 7 is provided to illustrate that increasing the number of independently controlled shells (herein 2 to 4) does decrease the ramping (i.e., slope angle α) of rotational velocity. One skilled in the art would appreciate that a variety of speed profiles may be used to accomplish a particular purpose. Examples and technical explanations of speed profiles may be found in Machinery's Handbook, 26th Edition, authored by Erik Oberg, published by Industrial Press Inc., New York, N.Y., copyright 2000; U.S. patent application Publication No. 2002/0023723A1; and U.S. Pat. No. 6,450,321. One skilled in the art would also appreciate that speed profiles could have a variety of different shapes, for instance, in order to run at a non-optimal radius as exampled in the aforementioned references.

It should be appreciated that the first and second surface speeds of said shells may be substantially constant (typical situation, wherein, the shell surface speeds match the material web and carrier speeds respectively). Alternatively, the first and second surface speeds of said shells may be variable (for example, stretching an elastic discrete part 25 either while it is in the receiving zone or while it is being applied onto the carrier 30). Alternatively, the first surface speeds of said shells or the second surface speeds of said shells may be variable.

Moreover, it should be appreciated that the speed profile for each motor of an apparatus 10 having four independently controlled shells 50 is representatively illustrated in FIG. 6. As shown, the programmable motor 60 which is used to drive the shells 50 can provide variable angular velocities including periods where the velocity remains constant for a fixed duration. These constant velocity dwell times can be advantageous in the receiving zone 23 and the application zone 27 particularly when the pick-up and transfer occurs over substantial arc lengths of contact. Alternatively, one or more of the constant speed regions can be changed to a controlled variable speed region. This would enable the discrete part 25 to be picked-up in the receiving zone 23 at a variable speed, which, when the part 25 is elastic, would allow tensions to be varied incrementally therein which may be desirous in certain product features. In another example, the constant speed of the motor 60 in the application zone 27 can be such that the corresponding speed of the shell 50 is different from speed of the carrier 30 at time of transfer. Such speed variations generate tension in discrete part 25 by incrementally transferring the part 25 in a controlled manner from shell 50 traveling at a first speed to the carrier 30 traveling at a second speed. It will be further appreciated that the velocity of shell 50 outside of the receiving zone 23 or the application zone 27 can be tailored to aid the performance of secondary processes including adhesive: application, printing of identification or registration marks, application of bonding aids, moisture addition and the like and combinations thereof. Such changes in velocity may be beneficial by presenting specific velocity profiles or even additional periods of constant velocity, which would allow for more precise interaction with the secondary processes being performed.

Referring back to FIGS. 1 and 4, because cutting blade 44 severs material web 20 against roll 80 and not shells 50, shells 50 may be lightweight and thin. Because shells 50 may be lightweight and thin, the torque imparted on their respective motors is significantly lowered thus making it easier to increase and decrease the shells' rotational velocity. Because the shells are easier to accelerate, the motors may be smaller in size which helps balance the delicate relationship described above.

Figures 8A, 8B:
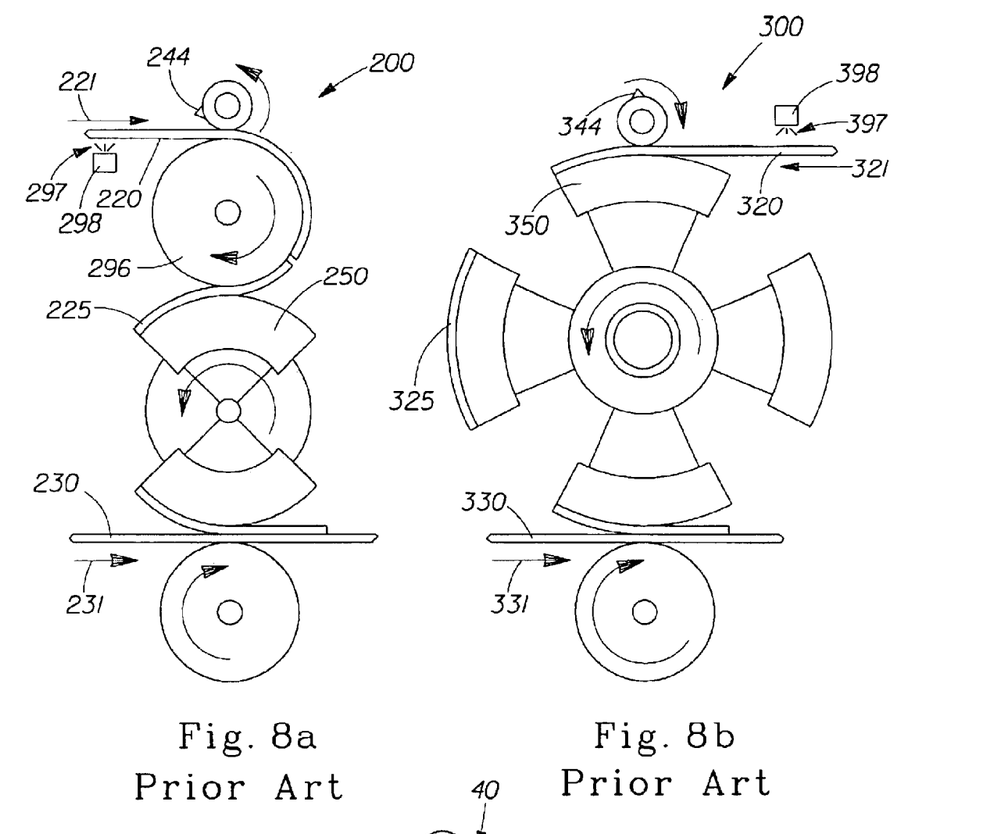
FIG. 8*a* representatively shows a schematic view of an apparatus in the prior art which cuts the material web against an anvil roll and experiences difficulties in applying continuous adhesive onto the material web.
FIG. 8*b* representatively shows a schematic view of an apparatus in the prior art which is capable of continuous adhesive application onto the material web, however, cuts the material web against its transfer heads.

Referring now to FIG. 8a, a first prior art apparatus 200 is shown, wherein, the cutting blade 244 severs the material web 220 against an anvil roll 296 and then the anvil roll 296 transfers discrete part 225 to a transfer head 250 for subsequent application onto carrier 230. While the use of anvil roll 296 instead of severing against transfer heads 250 allows for transfer heads 250 to be more lightweight (positive aspect as described above), the use of anvil roll 296 has difficulties in the continuous application of adhesive 297 to the material web 220 from an adhesive applicator 298 because the discrete part would adhere to transfer head 250.

Referring now to FIG. 8b, a second prior art apparatus 300 is shown, wherein, the cutting blade 344 severs the material web 320 directly against transfer head 350 and then applies discrete part 325 to carrier 330. While apparatus 300 allows for the continuous application of adhesive 397 to material web 320 from an adhesive applicator 398 apparatus, apparatus 300 does sever against transfer heads 350 which would require them to be sufficiently rigid to sustain the impact of cutting blade 344. Thus, apparatus 300 does require high torque as discussed above due to higher inertia needed to ensure sufficient stiffness.

Figure 8C:
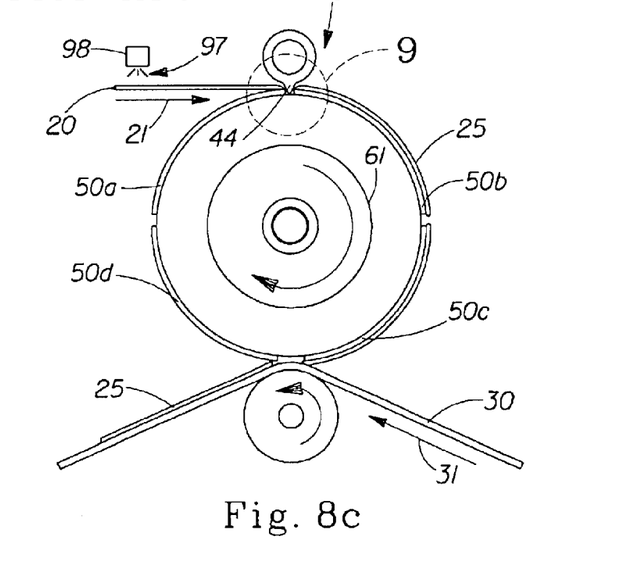
FIG. 8*c* representatively shows a schematic view of the apparatus in FIG. 1 with the addition of an adhesive applicator.

Referring now to FIG. 8c, this exemplary schematic view of the present invention illustrates that apparatus 10 is capable of both continuous application of adhesive 97 to material web 20 from an adhesive applicator 98 and not severing against shells 50 (analogous to transfer heads 250 and 350) which enables the use of smaller motors that fit well into the apparatus' mechanical design.

Additionally, an applicator for performing a secondary process on the parts between the receiving zone and the application zone may be used. An applicator for performing a secondary process on the parts before the receiving zone may also be used. The secondary process may be the application of adhesive or printing.

Figure 9:
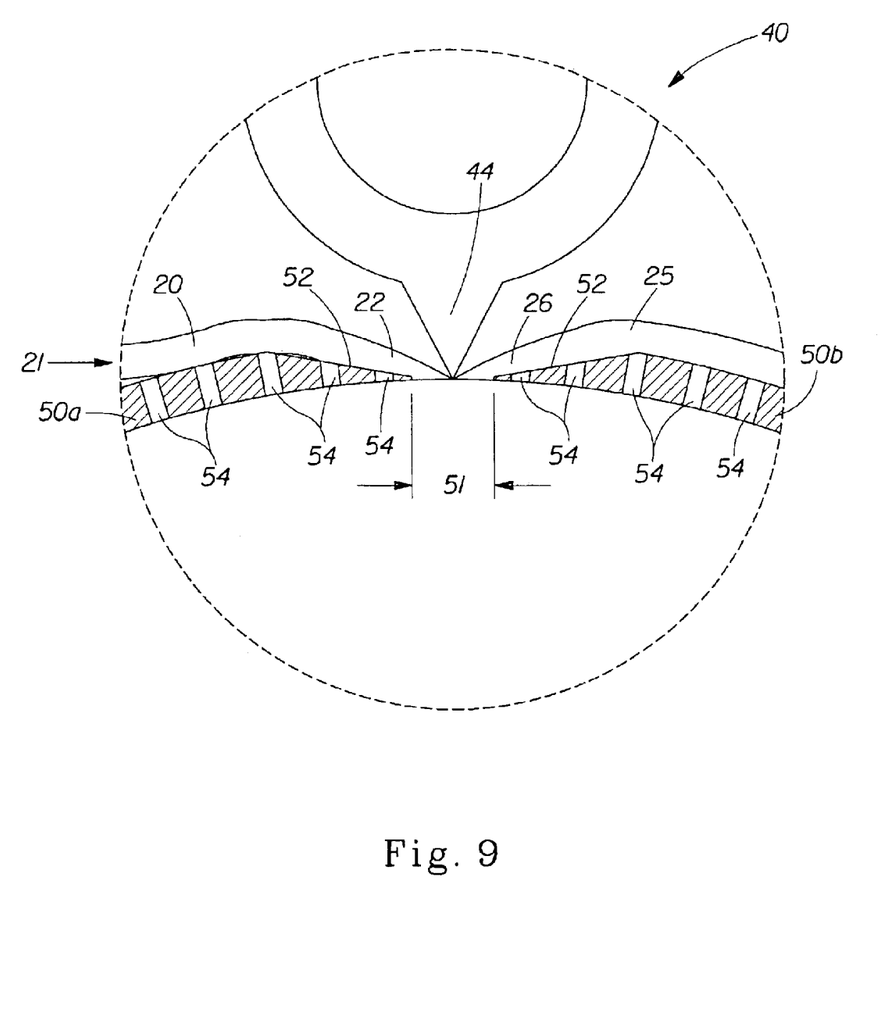
FIG. 9 representatively shows a close-up schematic view of the apparatus in FIG. 8.

Referring now to FIG. 9, a close-up schematic view of apparatus 10 taken from FIG. 8c, wherein, shells 50a and 50b are shown. Material web 20 is traveling in a direction indicated by arrow 21 and is severed by cutting blade 44 to subsequently become discrete part 25. To control any undesired movement of leading edge 22 of material web 20 and edges 26 of discrete part 25, shells 50a and 50b may have tapered ends 52. As discussed above, vacuum holes 54 may also be used to help secure discrete part 25 to shells 50. Vacuum holes 54 may also extended into tapered ends 52.

Another benefit of the present invention is that there is a wide range of acceptable ratios of the length of discrete parts 25 to the placement distance (defined as the distance between the leading edge of one discrete part 25 and the leading edge of the next discrete part 25 as measured on the carrier 30) of the discrete parts 25 onto carrier 30. For example, the length of discrete part 25 may be relatively small as compared to the placement distance, or it may be nearly as long as compared to the placement distance. This benefit arises from the low inertia of shells 50 which allows for high acceleration and deceleration within a reasonable torque limit. This benefit also arises from a high volume of space available for motor 60 due to the small thickness of shell 50. These benefits are especially appreciated when it is desired to run at a non-optimal radius ("radius" measured as the physical distance between the center of roll 80 and the outer surface of shell 50; "optimal" meaning that the resulting speed profile minimizes acceleration and deceleration).

Lastly, it should be appreciated that certain applications can benefit from having a flexible pitch capability. Typical examples of pitched systems include knife rolls, printing rolls, bonding rolls and the like, as well as the discrete parts transferring applications described herein. The pitch of a system such as a knife roll can be typically changed by adding additional tooling on a roll (e.g., the number of knives on a roll determines the number of pitches per a revolution of a roll), however such an approach is not convenient for a rapid change. Other alternatives can include varying the rotational speed of the roll, adding or subtracting spacer plates underneath the tooling to change radial distance from the axis of rotation, or operating the tooling at the appropriate cycle rate but a different surface speed from the substrate it is interacting with. The embodiments of the apparatus of the present invention can offer the benefit of matched speed interactions with the substrate at a desired cycle rate and without a need for physically modifying the system when changing from pitch length to pitch length, even if the pitch length varies either intentionally or unintentionally from product to product during continuous operation.

All patents, articles, documents, and other materials cited are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such combinations and modifications that are within the scope of this invention. For example, the actual location of receiving zone and application zone may be appreciated at other degrees around roll 80 and not limited to the embodiment shown in FIG. 5a. In another example, it should be appreciated that there is no restriction on the number of shells per motor besides space and inertial concerns, however, the arrangement pattern of multiple devices is limited. For instance, an apparatus having two shells per motor cannot be arranged such that any two shells on one motor are adjacent to one another in sequence without at least one shell from a separate motor interposed between them, as exampled in U.S. patent application Publication No. 2002/0023723A1.

What is claimed is:

1. An apparatus for receiving a material web traveling at a first speed in a receiving zone, forming discrete parts from the material web, and applying the discrete parts onto a carrier traveling at a second speed through an application zone, the apparatus comprising:

a cutting device for severing the material web to form the discrete parts;

at least two independent programmable motors;

at least two shells for receiving the discrete parts in the receiving zone and applying the discrete parts in the application zone, at least one of said shells being coupled to one of the programmable motors for moving said shell in an orbital path, wherein said programmable motors and said shells are aligned in relation to a common axis, wherein said programmable motors maintain said shells at first surface speeds in the receiving zone as said shells pick up the discrete parts and maintain said shells at second surface speeds in the application zone as said shells apply the discrete parts to the carrier; and a roll positioned interior to said shells, wherein the cutting device severs the material web between said shells and against said roll.

2. The apparatus of claim 1 wherein said roll is a vacuum roll, wherein said vacuum roll provides; vacuum in order to hold the discrete parts against said shells.

3. The apparatus of claim 1 wherein said cutting device is a cutting roll having an adjoining cutting blade which together rotates with or about a cutting roll shaft.

4. The apparatus of claim 1 wherein said cutting device rotates at a cutting surface speed substantially equal to a velocity of the material web while each of the discrete parts are being severed and formed and at a different cutting surface speed during intervals between discrete parts being severed and formed from the material web.

5. The apparatus of claim 1 wherein the first surface speeds of said shells are substantially equal to the first speed of the discrete parts in the receiving zone and the second surface speeds of the shells are substantially equal to the second speed of the carrier in the application zone.

6. The apparatus of claim 1 wherein at least one of the programmable motors is selected from the group consisting of a motor having a hollow shaft, a linear motor having a stationary track rail, a motor having a rotatable outer rotor and a stationary inner stator, and a motor having a rotor rotatable around a stationary component of a motor.

7. The apparatus of claim 1 wherein the programmable motors are located on at least one stationary central shaft coaxially with the common axis.

8. The apparatus of claim 1 wherein said shells have an axial length from about 4 cm to about 200 cm, tangential width from about 0.5 cm to about 200 cm, and a thickness from about 0.25 min to about 3 mm.

9. The apparatus of claim 1 wherein said shells are constructed from materials selected from the group consisting of plastic, aluminum, steel, and combinations thereof.

10. The apparatus of claim 1 wherein the shell holds the discrete parts by methods selected from the group consisting of vacuum, mechanical forces, electrostatic forces, magnetic forces, and combinations thereof.

11. The apparatus of claim 1 further comprising an applicator for performing a secondary process on the parts between the receiving zone and the application zone.

12. The apparatus of claim 1 further comprising an applicator for performing a secondary process on the parts before the receiving zone.

13. The apparatus of claim 12 wherein the secondary process is the application of adhesive or printing.

14. The apparatus of claim 1 wherein the shell has a tapered end.

15. The apparatus of claim 1 wherein the first and second surface speeds of said shells are substantially constant.

16. The apparatus of claim 1 wherein the first and second surface speeds of said shells are variable.

17. The apparatus of claim 1 wherein either the first surface speeds of said shells or the second surface speeds of said shells are variable.

18. The apparatus of claim 1 wherein the carrier is selected from the group consisting of a web substrate, belt, drum, and external-discrete part.

19. A method for receiving a material web traveling at a first speed in a receiving zone, forming discrete parts from the material web, and applying the discrete parts onto a carrier traveling at a second speed through an application zone, the method comprising the steps of:
  providing a cutting device for severing the material web to form the discrete parts;
  providing at least two independent programmable motors;
  providing at least two shells for receiving the discrete parts in the receiving zone and applying the discrete parts in the application zone, at least one of said shells being coupled to one of the programmable motors for moving said shell in an orbital path,
    wherein said programmable motors and said shells are aligned in relation to a common axis,
    wherein said programmable motors maintain said shells at first surface speeds in the receiving zone as said shells pick up the discrete parts and maintain said shells at second surface speeds in the application zone as said shells apply the discrete parts to the carrier;
  providing a roll positioned interior to said shells, wherein the cutting device severs the material web between said shells and against said roll;
  receiving the material web in the receiving zone;
  severing the material web between said shells and against said roll to form the discrete parts; and
  applying the discrete parts in the application zone.

20. The method of claim 19 wherein said roll is a vacuum roll, wherein said vacuum roll provides vacuum in order to hold the discrete parts against said shells.

* * * * *

UNITED STATES PATENT AND TRADEMARK OFFICE
CERTIFICATE OF CORRECTION

PATENT NO. : 6,811,019 B2
DATED : November 2, 2004
INVENTOR(S) : Christian et al.

It is certified that error appears in the above-identified patent and that said Letters Patent is hereby corrected as shown below:

Title page,
Item [63], Related U.S. Application Data, after "6,705,453", insert -- and application No. 10/197,023 filed July 17, 2002, now Pat. No. 6,814,217 --.

Column 7,
Line 33, delete "positions" and insert -- position --.

Column 8,
Line 55, delete "5a-d." and insert -- 50a-d. --.

Column 10,
Line 51, delete "adhesive:" and insert -- adhesive --.

Column 13,
Line 2, delete "provides;" and insert -- provides --.
Line 30, delete "min" and insert -- mm --.

Signed and Sealed this

Sixth Day of December, 2005

JON W. DUDAS
*Director of the United States Patent and Trademark Office*